United States Patent [19]

Sierocuk et al.

[11] Patent Number: 5,607,441
[45] Date of Patent: Mar. 4, 1997

[54] SURGICAL DISSECTOR

[75] Inventors: Thomas J. Sierocuk, West Chester; William A. Garrison, Cincinnati; Allan R. Michetti, Loveland, all of Ohio

[73] Assignee: Ethicon Endo-Surgery, Inc., Cincinnati, Ohio

[21] Appl. No.: 410,438

[22] Filed: Mar. 24, 1995

[51] Int. Cl.⁶ ............................................. A61B 17/00
[52] U.S. Cl. .................... 606/190; 606/192; 606/198; 604/96; 600/207
[58] Field of Search .................... 600/207, 209; 606/185, 197, 198, 190, 191; 604/264, 96

[56] References Cited

U.S. PATENT DOCUMENTS

| | | |
|---|---|---|
| 3,100,482 | 8/1963 | Hett . |
| 3,690,769 | 9/1972 | Mori ............................................ 356/41 |
| 4,779,611 | 10/1988 | Grooters et al. . |
| 4,794,911 | 1/1989 | Okada ...................................... 600/127 |
| 5,188,596 | 2/1993 | Condon et al. ...................... 606/192 X |
| 5,197,971 | 3/1993 | Bonutti ................................... 606/192 |
| 5,269,753 | 12/1993 | Wilk ........................................ 604/49 |
| 5,271,380 | 12/1993 | Riek et al. ................................. 128/4 |
| 5,307,814 | 5/1994 | Kressel et al. ........................... 606/192 |
| 5,309,896 | 5/1994 | Moll et al. ................................. 128/20 |
| 5,334,150 | 8/1994 | Kaali ...................................... 606/185 |
| 5,359,995 | 11/1994 | Sewell, Jr. ........................... 606/192 X |
| 5,402,788 | 4/1995 | Fujio et al. ........................... 128/653.2 |
| 5,496,345 | 3/1996 | Kieturakis et al. ..................... 606/192 |

FOREIGN PATENT DOCUMENTS

WO92/21295  12/1992  WIPO .
WO93/09722  5/1993  WIPO .
WO93/24172  12/1993  WIPO .

OTHER PUBLICATIONS

Spacemaker™ II Surgical Balloon Dissector, General Surgical Innovations, Inc., Palo Alto, California, 1994.

Primary Examiner—Michael Powell Buiz
Assistant Examiner—Patrick W. Rasche

[57] ABSTRACT

A surgical instrument having an elongated shaft to which is attached an inflatable balloon, commonly referred to a "balloon dissector", for dissecting a desired layer of internal bodily tissue from remaining tissue layers to create an operative space is disclosed. Alternatively, an instrument without a balloon can be used to perform a manual dissection. In one embodiment, the instrument has a tissue-contacting element in communication with the shaft distal end, and at least a portion of the tissue-contacting element is transparent. The instrument is adapted to receive an endoscope through its shaft and extend to adjacent the tissue-contacting element. The endoscope is supported and positioned in an extension assembly. The instrument provides for visualization using the endoscope as the instrument is advanced through tissue, but prevents direct contact between the tip of the endoscope containing the lens and the tissue. The extension assembly also enables the endoscope to be adequately positioned and supported beyond the shaft distal end. When the instrument incorporates the balloon, the endoscope can extend into the lumen of the inflated balloon. In this way, improved visualization during use can be obtained.

5 Claims, 7 Drawing Sheets

SURGICAL DISSECTOR

BACKGROUND OF THE INVENTION

This invention relates generally to a surgical instrument for creating an operative space during surgery. More specifically, it relates to such an instrument which creates this space by dissecting a desired layer of tissue from remaining tissue layers.

Tissue dissection to create space at a desired surgical site has been a focus of design engineers concentrating on the development of new surgical instrumentation. An increasingly popular method to dissect tissue involves inflating a balloon between adjacent tissue layers to separate those layers and create the desired space. Surgical procedures and instruments incorporating an inflatable balloon to carry out these procedures are described in U.S. Pat. Nos. 5,309,896 and 5,269,753; and published PCT International Application Nos. WO 92/212 95 and WO 93/097 22. Alternatively, dissection can be carried out manually without the aid of an inflatable balloon.

Another recent development in connection with surgical instruments is described in U.S. Pat. Nos. 5,271,380 and 5,334,150. These patents describe trocars for the penetration of bodily tissue. Unlike a conventional trocar in which the penetration of the tissue is performed blindly, the trocars described in these patents enable the user to simultaneously visualize the penetration of tissue as the trocar is advanced through the body wall. Trocars which enable simultaneous visualization are now referred to as "optical trocars". An optical trocar consists of a rigid tubular shaft to which is attached a transparent penetrating window. An endoscope for illuminating the surgical site and transmitting images of the site to the surgeon is received in the tubular shaft and extends adjacent the transparent penetrating window.

Unfortunately, the optical trocar described in the patents above may not always be ideal for creating needed operative space by carefully dissecting adjacent layers of tissue. In addition, the balloon dissectors currently available do not provide for simultaneous visualization as the surgeon is dissecting tissue.

Recently, General Surgical Innovations ("GSI") has shown a prototype product of what it refers to as the SPACEMAKER™ II Surgical Balloon Dissector. This dissecting instrument consists of a rigid hollow shaft to which is attached an inflatable balloon. The endoscope is insertable through the shaft, and the brochure accompanying this developmental instrument indicates that the endoscope is capable of providing for visualization during insertion as well as during balloon dissection. Unfortunately, when the endoscope may be inserted through the hollow shaft, the lens on the tip of the endoscope may be exposed to direct tissue contact as the instrument is advanced during insertion. The direct contact between the endoscope lens with the tissue and the lack of separation between them causes a significant deterioration of the visual capabilities of the endoscope, and therefore fails to satisfactorily address the problem of providing adequate visualization during the advancement of a balloon dissector. In addition, the position of the endoscope in relation to the inflated balloon is undesirable for optimum viewing. This is so because the endoscope is not readily supportable and positionable into and through a significant portion of the inflated balloon.

In view of these deficiencies inherent in the surgical instruments described in the references above, the surgical community needs a balloon dissector which satisfactorily enables the user to visualize during insertion, and to dissect the tissue when the balloon is inflated. The surgical community also needs an instrument which includes an elongate hollow shaft for receiving an endoscope to provide visualization during surgery, but also enables the user to position and support the endoscope significantly beyond the distal end of the shaft for optimum viewing.

SUMMARY OF THE INVENTION

In one aspect of the invention, the invention is a surgical instrument comprising an elongated tubular shaft having a distal end and a shaft longitudinal axis. A tissue-contacting element is in communication with the shaft distal end, and at least a portion of this element is transparent. An inflatable transparent balloon is attached to the shaft.

The surgical instrument of this invention enables the user to not only dissect tissue when the balloon is inflated, but also visualize the tissue as the instrument is advanced when an endoscope is positioned adjacent to the tissue-contacting element for viewing. Unlike GSI's SPACEMAKER™ II Surgical Balloon Dissector which may allow for direct contact between the endoscope lens and instrument tissue when the instrument is advanced, the device of this invention incorporates a tissue-contacting element preventing direct contact between the tip of the endoscope and the tissue. Since at least a portion of the tissue-contacting element is transparent, an endoscope inserted through the tubular shaft can transmit illuminated images received from the surgical site through the transparent portion of the window without requiring direct contact of the endoscope lens with the tissue.

In another aspect of the invention, the invention is a surgical instrument for dissecting internal bodily tissue. The instrument comprises a trocar cannula and an extension assembly. The trocar cannula has a cannula housing and an elongated tubular sleeve extending distally from the housing. The trocar cannula is adapted to slidably receive an endoscope through the housing and tubular sleeve. The tubular sleeve has a longitudinal axis and a distal end.

The extension assembly is connected to the distal end of the sleeve and extends distally from the sleeve distal end. The assembly has a proximal end affixed to the sleeve distal end and a distal end having a restricting member positioned remote from the sleeve distal end. A plurality of spaced apart extender arms connect the assembly proximal end to the assembly distal end. The extender arms extend in a direction generally parallel to the longitudinal axis of the sleeve. The extension assembly provides a passageway through it from the sleeve distal end between the extender arms to the assembly distal end for receiving and supporting an endoscope inserted through the assembly for positioning adjacent the restricting member.

Significantly, the extension assembly connected to the trocar cannula of the surgical instrument of this invention provides a supporting structure for an endoscope which is inserted through the trocar cannula and extends well beyond the distal end of the tubular sleeve of the cannula. The restricting member at the distal end of the extension assembly provides a positive stop to prevent further distal movement of the endoscope beyond the restricting member, and therefore facilitates the precise positioning of the endoscope during the tissue dissection procedure. In one preferred embodiment, an inflatable balloon is affixed to the distal end of the tubular sleeve of the trocar cannula and surrounds the extender arms and the restricting member of the extension assembly. This preferred instrument can then be used as a balloon dissector, and it has the advantage of enabling the user to supportably extend the endoscope significantly beyond the distal end of the tubular sleeve and into and through the lumen of the inflatable balloon. The comprehensiveness of the visual field and the visual acuity obtained when the endoscope is positioned in this way during a tissue dissection is significantly greater than that obtained using other balloon dissectors which have recently entered the public domain.

The surgical instruments of this invention can be used in any procedure where it is desirable to inflate a balloon to provide for the dissection of bodily tissue. Alternatively, they can be used to perform a manual dissection without the aid of a balloon where it is desirable to provide enhanced simultaneous visualization. The instruments can be used in conventional as well as endoscopic surgical procedures, although the instrument is particularly adapted for endoscopic surgical procedures such as laparoscopic hernia repair, laparoscopic bladder neck suspension, and lymph node dissections.

DETAILED DESCRIPTION OF THE PREFERRED EMBODIMENT

Figure 1:
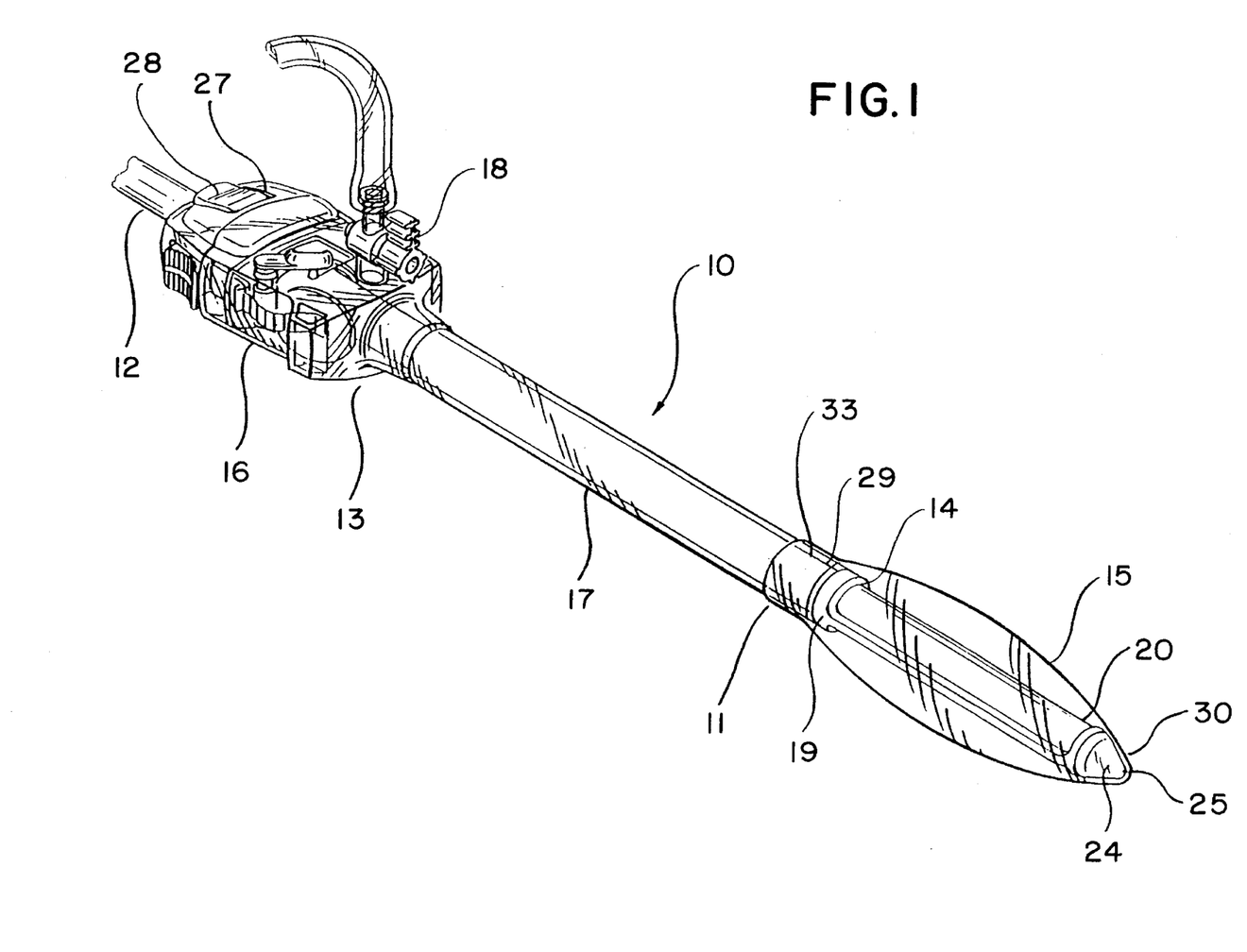
FIG. 1 is a perspective of an assembly including the surgical instrument of this invention configured as a balloon dissector shown in a deflated position.
Figure 2:
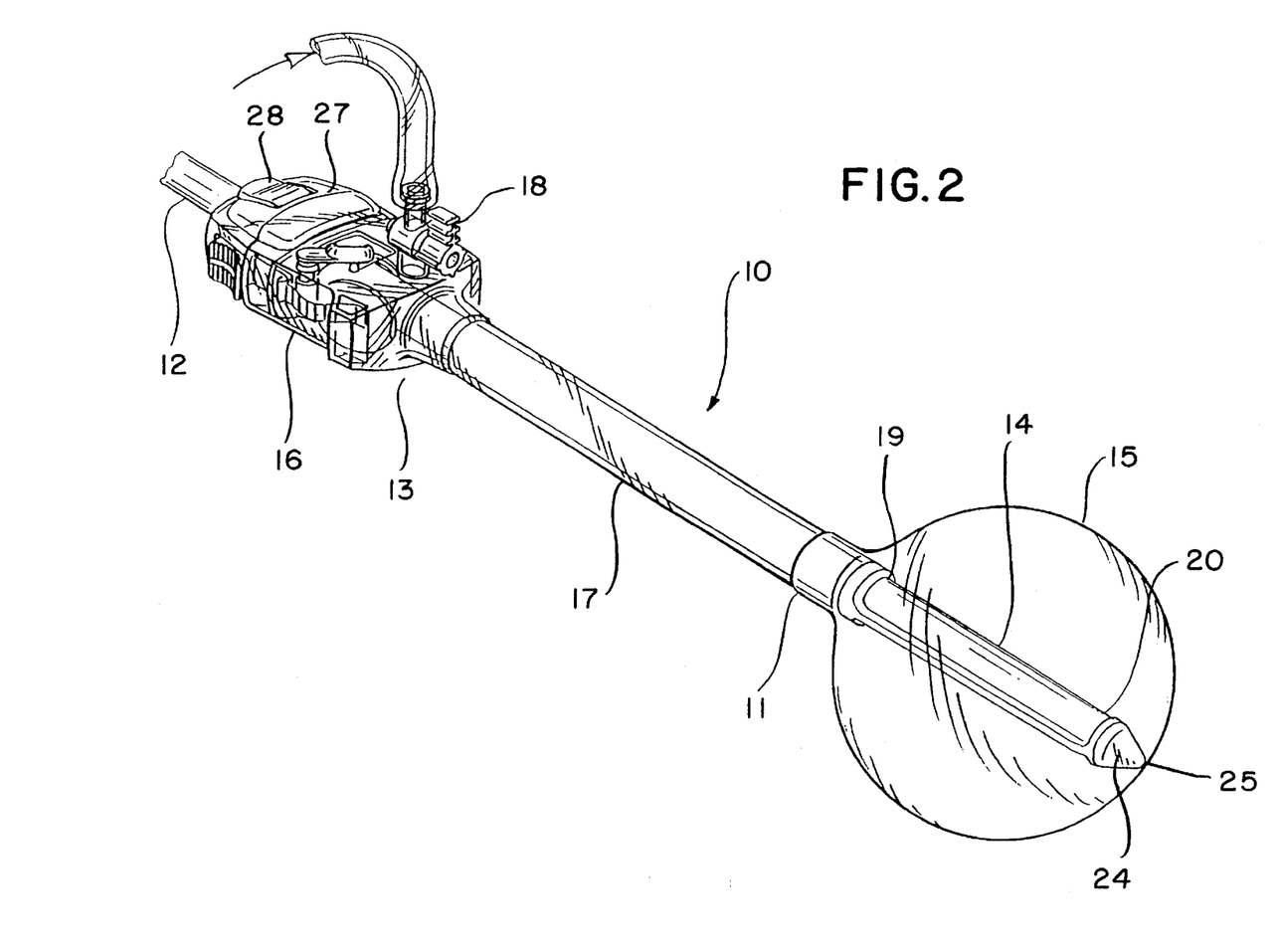
FIG. 2 is a perspective view of the assembly where the balloon dissector is shown in an inflated position.
Figure 3:
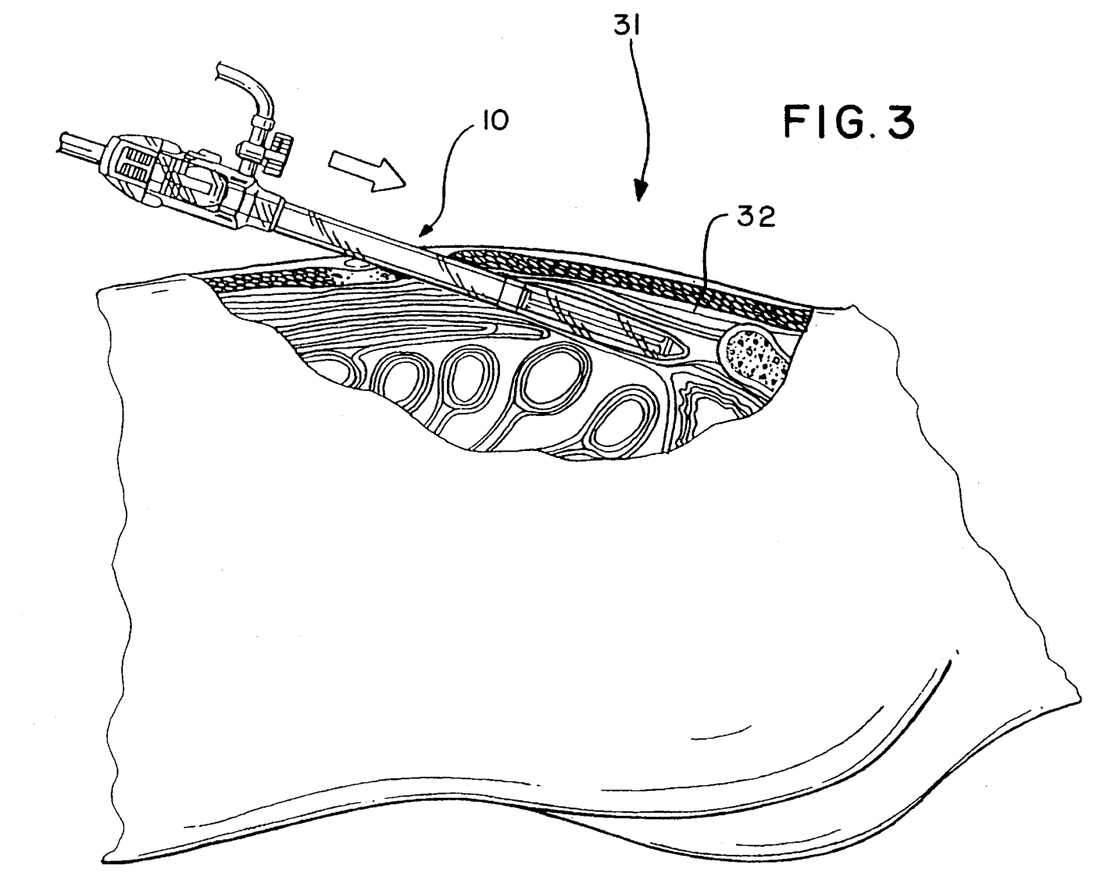
FIGS. 3–5 are side elevational views, partially broken away, showing how the assembly is used to dissect internal layers of tissue to create an operative space on a surgical patient.
Figure 4:
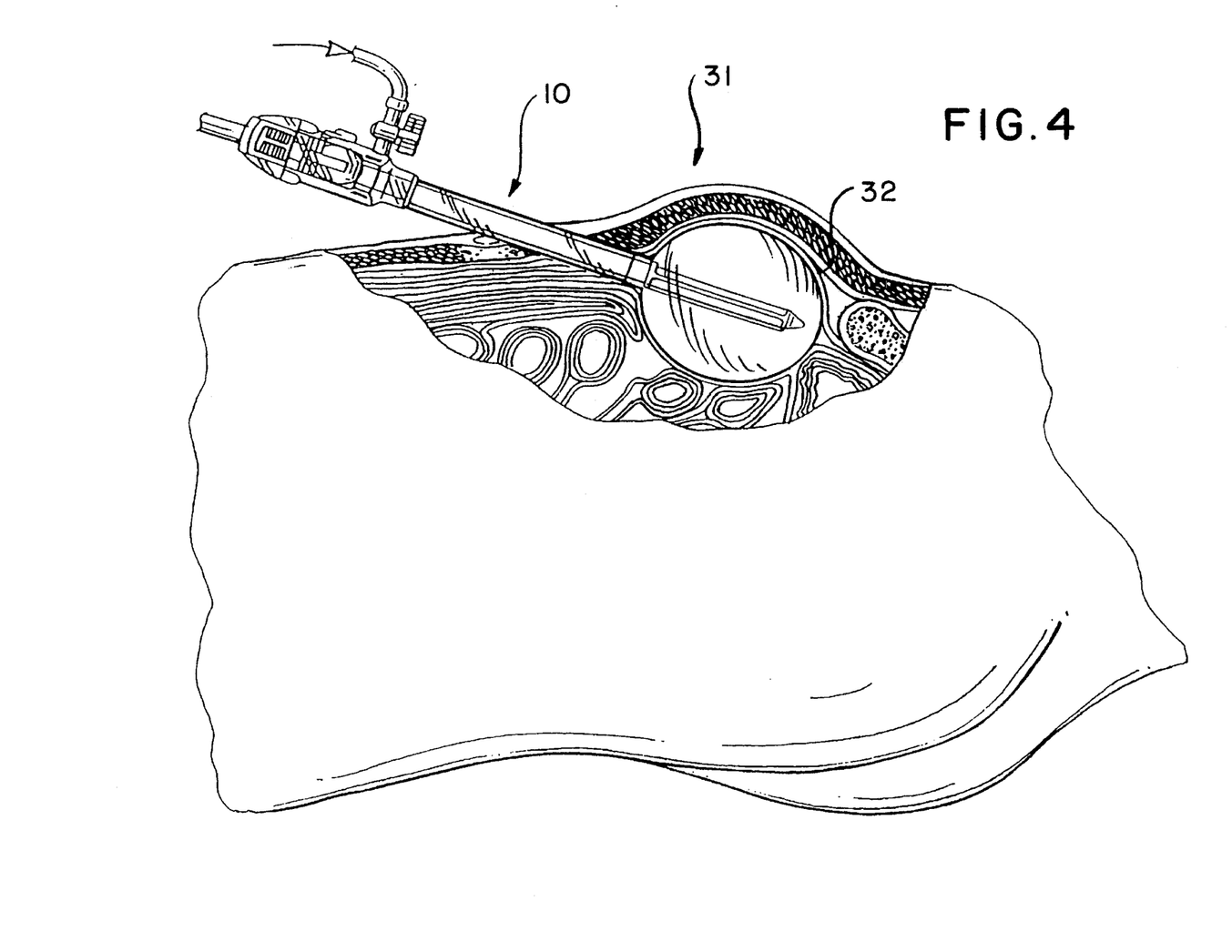
Figure 5:
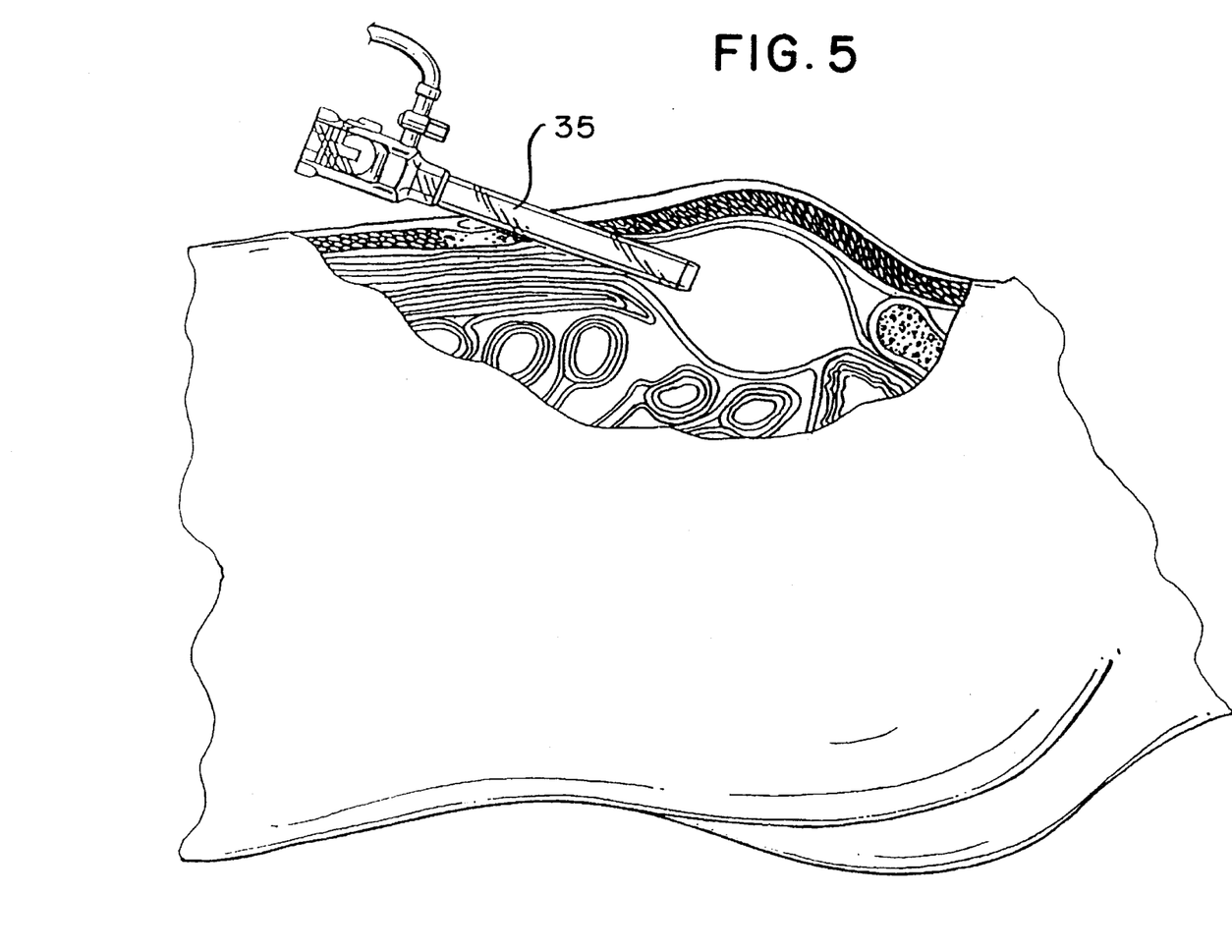
Figures 7, 8, 9:
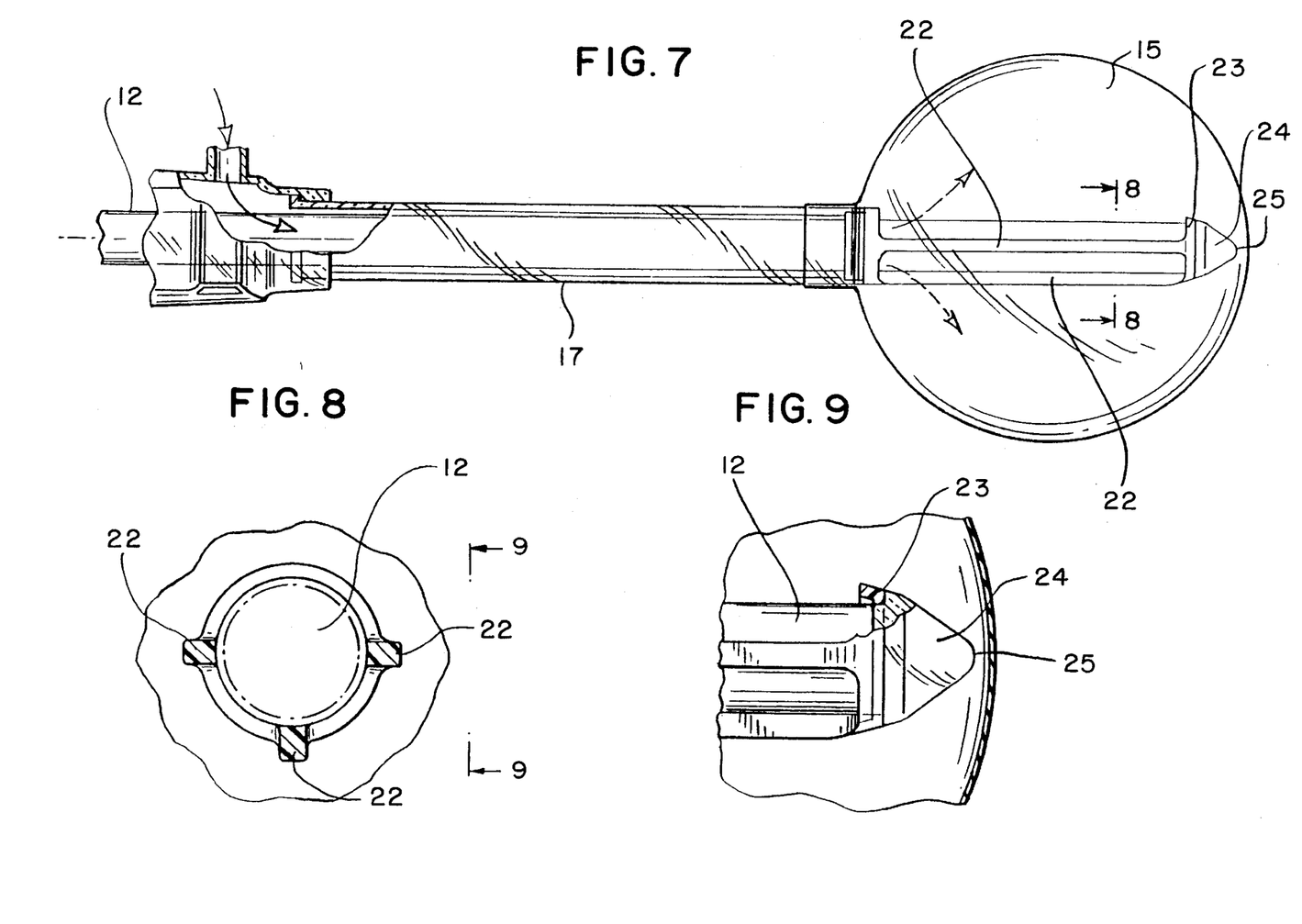
FIG. 7 is a partial side elevational view of the assembly with portions broken away to disclose the method of inflating the balloon dissector.
FIG. 8 is a cross-sectional view of the extender arms of the extension assembly which forms a part of the preferred balloon dissector as taken along section line 8—8 of FIG. 7.
FIG. 9 is an enlarged side view illustrating the abutting relationship between the distal end of the endoscope and the restricting member at the distal end of the extension assembly as seen along view line 9—9 of FIG. 8.

The preferred surgical instrument of this invention includes an assembly 10 having a balloon dissector 11 as the primary component. The assembly is best illustrated in FIGS. 1, 2, and 7. The assembly consists of two primary components. These components are the balloon dissector 11 for the dissection of internal bodily tissue to create an operative space during a surgical procedure, and an endoscope 12 in cooperation with the balloon dissector to provide simultaneous visualization during the surgical procedure as the dissector is advanced through tissue and the operative space is created.

Figure 6:
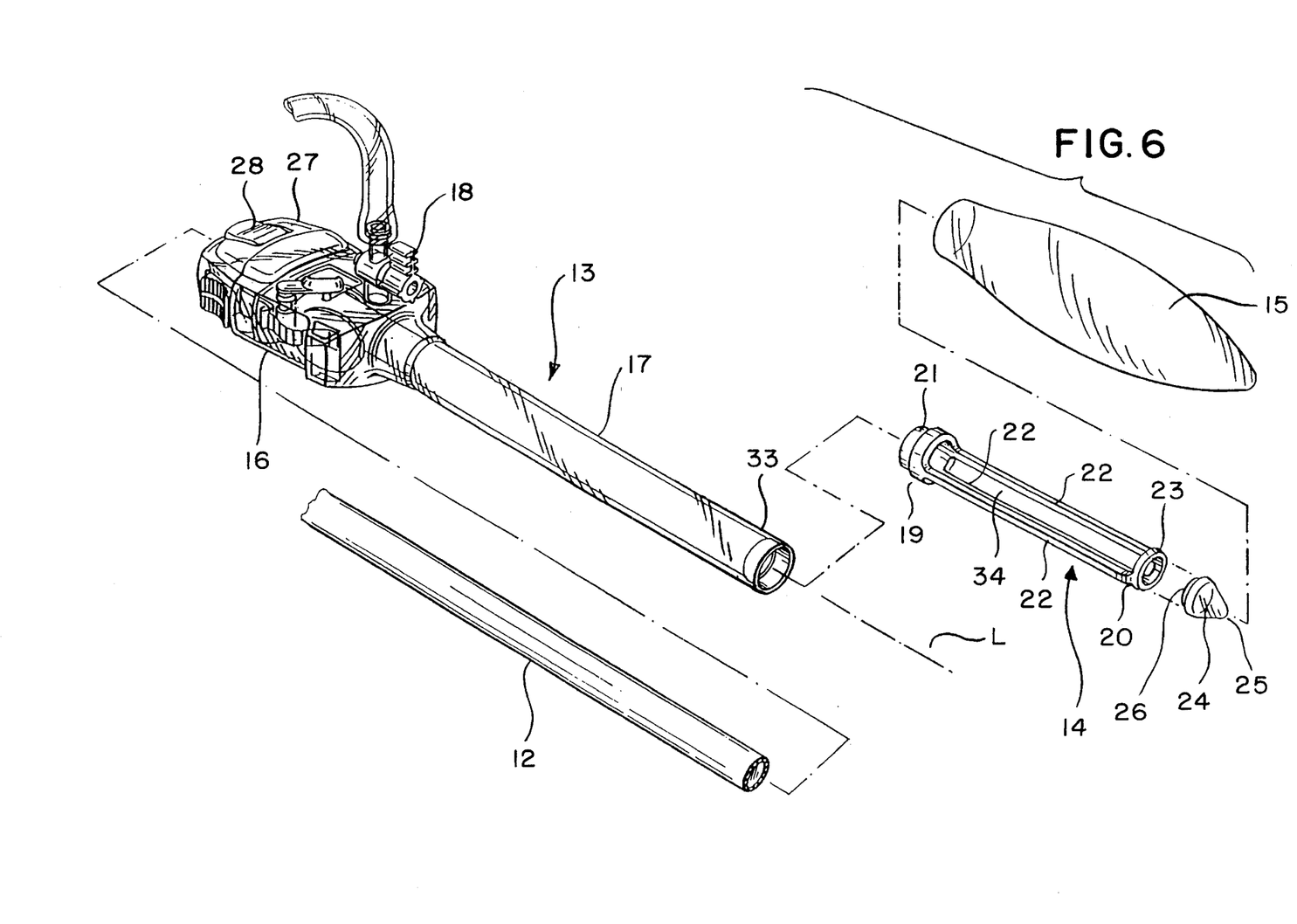
FIG. 6 is an exploded perspective view of the assembly.

The balloon dissector consists of a conventional trocar cannula 13, an extension assembly 14 to position and provide support for an endoscope, and an inflatable balloon 15. The trocar cannula has a cannula housing 16 providing a passageway to an elongated tubular sleeve 17 extending distally from the housing. The housing contains a conventional stop-cock valve 18 to selectively provide for the flow of a pressurized fluid such as air from a suitable external source through the housing and sleeve into the balloon. The tubular sleeve 17 of the cannula is sized to slidably receive an endoscope. The sleeve has a distal end 33, and the sleeve defines a longitudinal axis designated as "L" in FIG. 6.

The extension assembly 14 is attached to the distal end of the tubular sleeve of the cannula. The extension assembly has proximal and distal ends, 19 and 20, respectively, and provides a passageway 34 from the proximal end to the distal end to receive, position and support the endoscope 12 protruding from the distal end of the tubular sleeve. The assembly proximal end is shaped as a short tube 21 which can be removably or permanently secured within the internal diameter of the tubular sleeve as illustrated in FIG. 7. Alternatively, it can be secured externally to the outer diameter of the sleeve.

Three extender arms 22 extend from the short tube 21 at the proximal end of the extension assembly and terminate at the distal end of the extension assembly. Although three arms are shown, it may be desirable to construct the extension assembly with four arms to provide enhanced support without appreciably sacrificing optical quality during visual observation using the endoscope. The extender arms 22 are displayed generally parallel to the longitudinal axis L of the tubular sleeve of the cannula, and therefore do not obstruct the passageway when the endoscope is inserted into and through the extension assembly.

The extension assembly is desirably composed of a resilient plastic so that the extender arms provide resiliency without sacrificing needed support. This resiliency in turn provides needed flexibility as the instrument is advanced during surgery. The extender arms are connected at the distal end of the extension assembly with a restricting member in the form of a ring 23. The ring has an internal diameter smaller than the internal diameter of the tubular sleeve of the cannula and of the endoscope 12. The ring therefore blocks distal movement of the endoscope at the distal end of the extension assembly to facilitate the desired positioning of the endoscope (see FIG. 9).

In one preferred embodiment, a tissue-contacting element 24 is fastened to the distal end 20 of the extension assembly adjacent the ring 23. The tissue-contacting element is a transparent, hollow cone which acts as a window for the endoscope and helps to prevent direct contact between the endoscope and internal bodily tissue as the instrument is advanced during a surgical procedure. The cone has a blunt tip 25 to ensure atraumatic blunt tissue dissection and is positioned on the extension assembly so that it is symmetrical about the longitudinal axis of the tubular sleeve.

The endoscope is a conventional, fully-integrated rigid endoscope which provides the delivery of light into the body from an external source and transmits images from the illuminated body cavity to the surgeon at an eye piece or a video monitor, whichever is desirable. The endoscope is releaseably inserted into the trocar cannula and through the tubular sleeve of the cannula. It protrudes beyond the sleeve distal end into the passageway and structural support provided by the extension assembly. In this particular embodiment, the endoscope can be inserted distally until it abuts not only the ring 23 at the distal end of the extension assembly, but also an internal annulus 26 of the tissue-contacting element adjacent the ring. When a light source is activated, the light is delivered through the endoscope and exits the distal end of the endoscope. The light travels through the transparent conical window of the tissue-contacting element and is emitted into the body cavity to provide illumination.

The illuminated images from the body cavity are reflected back through the window and are transmitted through the endoscope to provide the surgeon with the illuminated images in the conventional manner. The endoscope is securely supported and positioned within the extension assembly, and the tissue-contacting element provides a barrier between the tissue as it is being dissected and the distal end of the endoscope.

To provide further support and precise positioning of the endoscope within the extension assembly, the trocar housing 16 includes a locking assembly 27 affixed to the cannula housing 16. The locking assembly has a latch 28 to secure the endoscope in a desired position during use. This locking assembly is described in more detail in co-pending application Ser. No. 08/382,462, filed Feb. 1, 1995.

The last component of the assembly incorporating the balloon dissector is, of course, the inflatable balloon 15. The balloon is preferably made of a puncture-resistant, distensible material compatible with human tissue. Preferably, the balloon is composed of a silicone elastomer. The balloon has a proximal end 29 affixed to the distal end of the tubular sleeve of the cannula. Alternatively, if the extension assembly 14 is affixed to the outer diameter of the tubular sleeve, then the proximal end of the balloon can be attached to the extension assembly proximal end. The proximal end of the balloon can be attached using conventional methods such as heat sealing. The extension assembly and the tissue-contacting element protrude into the lumen of the balloon, and therefore the balloon completely surrounds and envelopes these components. The distal end of the balloon 30 fits snugly over the tissue-contacting element when the balloon is in a deflated position.

As illustrated in FIG. 7, the balloon is inflated when the stop-cock valve mounted on the trocar cannula is turned on to permit the passage of pressurized air in the direction of the arrows through the tubular sleeve and into the lumen of the balloon to inflate the balloon. Once the balloon is inflated, the stop-cock valve is turned off, and the balloon will maintain its inflated condition until it is desired to deflate the balloon. At this point, the source of pressurized air is removed, and the stop-cock valve is once again turned on to allow the air inside the inflated balloon to escape through the tubular sleeve and out of the stop-cock valve of the trocar cannula. Although the inflated balloon is illustrated as a spherical balloon, other desired shapes can be used, and the shape of the balloon is not an essential feature of this invention.

In an alternative embodiment (not shown), the assembly does not include the tissue-contacting element, and the endoscope simply abuts only the ring at the distal end of the extension assembly for desired support and positioning of the endoscope.

The use of the assembly including the balloon dissector during a surgical procedure to dissect internal bodily tissue for the creation of an operative space is illustrated in FIGS. 3–6. An exposed portion of a surgical patient 31 is illustrated. The exposed portion of the patient includes internal layers of bodily tissue 32. To dissect away certain layers of the tissue from other layers, the assembly is inserted through the outer layers of the skin and advanced in a direction generally parallel to the adjacent layers of the internal bodily tissue. Concurrently with the advancement of the assembly through the tissue, the surgeon will visualize the advancement using the endoscope. Once the surgeon has advanced the assembly to the desired position within the bodily tissue, the balloon is inflated through the cannula sleeve to further separate the adjacent layers of tissue. Significantly, the protrusion of the endoscope well beyond the sleeve distal end into and through the extension assembly greatly enhances the visual field for the surgeon as the dissection progresses. The visual clarity and comprehensiveness of the visual field is appreciably greater than what it would be if the endoscope did not extend beyond the sleeve distal end, or if the extension assembly were replaced with a tubular extension.

After the balloon is sufficiently inflated to separate the tissue, the balloon is then deflated. The assembly including the balloon dissector may then be removed from the patient, and another trocar cannula 35 can be introduced into the patient where the space has been created (see specifically FIG. 5). The surgeon can then perform therapeutic or diagnostic procedures within the operative space created using the new trocar cannula as a passageway for other surgical instruments.

This invention has been described in connection with a specific preferred embodiment. The descriptions provided to illustrate this embodiment should not be used as a basis for a narrow or limited construction of the language set forth in the appended claims. Quite the contrary, the appended claims should be interpreted broadly because one skilled in this art can readily envision numerous additional embodiments which have not been specifically described but nevertheless would fall within the scope and spirit of the claimed invention.

What is claimed is:

1. A surgical instrument for dissecting internal bodily tissue, said instrument comprising:

a trocar cannula having a cannula housing and an elongate tubular sleeve extending distally therefrom for slidably receiving an endoscope therethrough, said tubular sleeve having a longitudinal axis and a distal end; and an extension assembly connected to said sleeve distal end and extending distally therefrom, said assembly having a proximal end affixed to said sleeve distal end and a distal end having a restricting member positioned remote from said sleeve distal end, and a plurality of spaced apart extender arms connecting said assembly proximal end to said assembly distal end, said extender arms extending in a direction generally parallel to said sleeve longitudinal axis, wherein said extension assembly provides a passageway therethrough from said sleeve distal end between said extender arms to said assembly distal end for receiving and supporting an endoscope inserted through said assembly for positioning adjacent said restricting member, said restricting member blocking distal movement of said endoscope beyond said restricting member.

2. The instrument of claim 1 wherein said sleeve has an outer diameter, and said restricting member is in the form of a ring having a ring diameter less than said sleeve outer diameter.

3. The instrument of claim 2 wherein said extension assembly has no more than four extender arms.

4. The instrument of claim 3 further comprising an inflatable balloon surrounding said extender arms and said restricting member.

5. The instrument of claim 4 wherein said balloon has proximal and distal ends, said balloon proximal end is attached to said assembly proximal end, and said balloon distal end is in contact with said restricting member when said balloon is in a deflated condition.

* * * * *